United States Patent [19]

Douglas et al.

[11] Patent Number: 5,596,113

[45] Date of Patent: Jan. 21, 1997

[54] RUTHENIUM-PHOSPHINE COMPLEX CATALYSTS FOR ASYMMETRIC HYDROGENATIONS

[75] Inventors: Alan W. Douglas, Monmouth Junction; Lisa DiMichele, Plainfield; Steven A. King, Summit; Thomas R. Verhoeven, Cranford, all of N.J.

[73] Assignee: Merck & Co., Inc., Rahway, N.J.

[21] Appl. No.: 443,614

[22] Filed: May 18, 1995

Related U.S. Application Data

[60] Division of Ser. No. 177,481, Jan. 5, 1994, Pat. No. 5,508, 435, which is a continuation-in-part of Ser. No. 922,355, Jul. 13, 1992, abandoned.

[51] Int. Cl.$^6$ ................................................. C07F 15/00
[52] U.S. Cl. ................................................................ 556/14
[58] Field of Search ................................................ 556/14

[56] References Cited

U.S. PATENT DOCUMENTS

| | | | |
|---|---|---|---|
| 4,933,482 | 6/1990 | Sayo et al. | 558/252 |
| 4,954,644 | 9/1990 | Sayo et al. | 556/14 |

FOREIGN PATENT DOCUMENTS

| | | |
|---|---|---|
| 0295109 | 12/1988 | European Pat. Off. . |
| 0484271 | 5/1992 | European Pat. Off. . |
| 0105421 | 2/1977 | Japan . |

OTHER PUBLICATIONS

"BINAP: An Efficient Chiral Element for Asymmetric Catalysis", Noyori, et al., Acc. Chem. Res., vol. 23, pp. 345–350 (1990).

"Convenient Preparation of Binap–Ruthenium(II) Complexes Catalyzing Asymmetric Hydrogenation of Functionalized Ketones", Kitamura, et al., Tetrahedron Letters, vol. 32(33), pp. 4163–4166 (1991).

"Enantioselective Reduction of β–Keto Esters", Taber, et al., Tetrahedron Letters, vol. 32(34), pp. 4227–4230 (1991).

"Total Synthesis of (–)–Colletol", Keck and Murry, J. Org. Chem., vol. 56, pp. 6606–6611 (1991).

"Asymmetric Hydrogenation of β–Keto Carboxylic Esters. A Practical, Purely Chemical Access to Beta–Hydroxy Esters in High Enantiomeric Purity", Noyori, et al., J. Am. Chem. Soc., vol. 109, pp. 5856–5858 (1987).

"Studies Relating to the Synthesis of the Immunosuppressive Agent FK–506: Coupling of Fragments via a Stereoselective Trisubstituted Olefin Forming Reaction Sequence", Jones, et al., J. Org. Chem., vol. 54, pp. 17–19 (1989).

"A Practical Asymmetric Synthesis of Carnitine", Kitamura, et al., Tetrahedron Letters, vol. 29(13), pp. 1555–1556 (1988).

"Synthesis of Statine and its Analogues by Homogeneous Asymmetric Hydrogenation", Nishi, et al., Tetrahedron Letters, vol. 29(48), pp. 6327–6330 (1988).

"Structural and Synthetic Studies of the Spore Germination Autoinhibitor Gloeosporone", Schreiber, et al., J. Am. Chem. Soc., vol. 110(18), pp. 6210–6218 (1988).

"Synthesis of Novel Chiral Ruthenium Complexes of 2,2′–Bis(diphenylphosphino)–1,1′–binaphthyl and their Use as Asymmetric Catalysts", Ikariya, et al., J. Chem. Soc., Chem. Commun., pp. 922–924 (1985).

"Formation of a Trimethyldihydroperimidinium Cation from Proton Sponge [1,8–Bis(dimethylamino)naphthalene] during Base–promoted Reactions of Rhodium and Ruthenium Complexes", Gamage, et al., J. Chem. Soc., Chem. Commun., pp. 894–895 (1987).

"Synthesis, Characterization and Reactivity of some Mono– and Dinuclear Chlororuthenium Complexes Containing Chelating Ditertiary Phosphines (P—P) with P—P:Ru=1", Joshi, et al., Inorg. Chimica Acta, 198–200, pp. 283–296 (1992).

"Enantioselective Synthesis of 4–Substituted γ–Lactones", Ohkuma, et al., Tet. Ltrs., vol. 31(38), pp. 5509–5512 (1990).

"Characterization and Properties of the Dinuclear Ruthenium Molecular Hydrogen Complex [(η$^2$–H$_2$)(dppb)Ru(µ–Cl)$_3$RuCl(dppb)]; dppb=Ph$_2$P(CH$_2$)$_4$PPh$_2$", Joshi and James, J. Chem. Soc., Chem. Commun., pp. 1785–1786 (1989).

"Enantioselective Ru–Mediated Synthesis of (–)–Indolizidine 223AB", Taber, et al., J. Org. Chem., vol. 57, pp. 5990–5994 (1992).

"Cyclopentane Construction with Control of Side Chain Configuration: Enantioselective Synthesis of (+)–Brefeldin A", Taber, et al., J. Am. Chem. Soc., vol. 113, pp. 6639–6645 (1991).

"Activation of Dihydrogen by Ruthenium(II)–Chelating Phosphine Complexes, and Activation of Dioxygen by Ruthenium(II) Porphyrin Complexes: An Update", James, et al., Journal Molecular Catalysis, vol. 41, pp. 147–161 (1987).

"Asymmetric Hydrogenation of 3–Oxo Carboxylates Using Binap–Ruthenium Complexes: (R)–(–)–Methyl 3–Hydroxybutanoate", Kitamura, et al., Org. Syn., vol. 71, pp. 1–13 (1992).

"Molecular Dihydrogen and Hydrido Derivatives of Ruthenium(II) Complexes Containing Chelating Ferrocenyl––Based Tertiary Phosphine Amine Ligands and/or Monodentate Tertiary Phosphine Ligands", Hampton, et al., Inorg. Chem., vol. 31, pp. 5509–5520 (1992).

"BINAP–Ruthenium(II) Dicarboxylate Complexes: New, Highly Efficient Catalysts for Asymmetric Hydrogenations", Ohta, et al., Inorg. Chem., vol. 27, pp. 566–569 (1988).

"Characterization and Reactivity of Di–µ–chloro–tetrahydridotetrakis–(triarylphosphine)–diruthenium(III) Complexes, Ru$_2$H$_4$Cl$_2$(PR$_3$)$_4$", Dekleva, et al., Inorg. Chimica Acta, vol. 100, pp. 49–56 (1985).

(List continued on next page.)

*Primary Examiner*—David B. Springer
*Attorney, Agent, or Firm*—Valerie J. Camara; Mark R. Daniel

[57] ABSTRACT

β- or γ-Ketoesters and β- or γ-ketoamides are asymmetrically reduced with a Ru(II)-BINAP derived catalyst at about 40° C. and about 50 N/mm$^2$ of hydrogen in the presence of a strong acid.

3 Claims, 2 Drawing Sheets

OTHER PUBLICATIONS

"Trichloro–Bridged Diruthenium(I,III) Complexes: Preparation, Properties, and X–ray Structure of $Ru_2Cl_5(chiraphos)_2$ (chiraphos=2(S), 3(S)–Bis(diphenylphosphino)butane)", Thorburn, et al., Inorg. Chem., vol. 25, pp. 234–240 (1986).

"The Dichlorobis(triphenylphosphine)ruthenium(II) Dimer", James, et al., Inorg. Chimica Acta, vol. 29, pp. L237–L–238 (1978).

"Molecular–Hydrogen, Nitrogen and Monohydride Derivatives of the Structurally Characterized Dichloro)o–diphenylphosphino–N,N–dimethylaniline)[tris(p–tolyl)phosphine]ruthenium(II) Complex", Mudalige, et al., J. Chem. Soc., Chem. Commun., pp. 830–832 (1993).

"Highly Stereoselective Asymmetric Hydrogenation of 2–Benzamidomethyl–3–oxobutanoate Catalysed by Cationic binap–Ruthenium(II) Complexes†", Mashima, et al., J. Chem. Soc., Chem. Commun., No. 9, pp. 609–610 (1991).

"Asymmetric Hydrogenation of Unsaturated Carbonyl Compounds Catalyzed by BINAP–Ru(II) Complexes. Enantioselective Synthesis of γ–Butyrolactones and Cyclopentanones", Ohta, et al., Tet. Ltrs., vol. 33(5), pp. 635–638 (1992).

"Synthesis of New Cationic BINAP–Ruthenium(II)Complexes and their Use in Asymmetric Hydrogenation [BINAP=2,2'–bis(diphenylphosphino)–1,1'binaphthyl]", Mashima, et al., J. Chem. Soc., Chem. Commun., pp. 1208–1210 (1989).

"Stereochemistry and Mechanism of the Asymmetric Hydrogenation of Unsaturated Carboxylic Acids Catalyzed by BINAP–Ruthenium(II) Dicarboxylate Complexes", Ohta, et al., Tet. Ltrs., vol. 31(49), pp. 7189–7192 (1990).

Takasago Int'l. Corp., "Asymmetric Synthesis: Asymmetric Hydrogenation Using BINAP–Complex Catalysts" (1993) Rockleigh N.J. 07647.

"A Molecular Dihydrogen Moiety within Dimeric Chlorohydrido(tertiary phosphine) Ruthenium Complexes", Hampton, et al., Inorg. Chimica Acta, vol. 145 pp. 165–166 (1988).

"Chemistry of the Transition Elements", Cotton and Wilkinson, Advance Inorg. Chem., 5 Edition, Wiley Inter. Sci., pp. 878–900 (1988).

"Asymmetric Catalysis by Chiral Metal Complexes", Noyori, Chemtech, pp. 360–367 (Jun. 1992).

"Homogeneous Asymmetric Hydrogenation of Functionalized Ketones", Kitamura, et al., J. Am. Chem. Soc., vol. 110, pp. 629–631 (1988).

RUTHENIUM-PHOSPHINE COMPLEX CATALYSTS FOR ASYMMETRIC HYDROGENATIONS

SUMMARY OF THE INVENTION

This is a division of application Ser. No. 08/177,481 filed Jan. 5, 1994, now U.S. Pat. No. 5,508,435, which is a CIP of Ser. No. 07/922,355, now abandoned, filed 13 Jul. 1992.

The present invention relates to a novel process in which it has been shown that in the presence of trace amounts of strong acid an asymmetric hydrogenation proceeds at low temperatures and readily attainable pressures with substrate/catalyst ratios up to about 10,000. The reaction can be carried out at pressures of less than or equal to 150 psi as such the reaction does not require special equipment to run the reaction and can be carried out on a pilot plant scale.

Another aspect of this invention is a simple reproducible procedure for preparation of purified catalyst. This invention also relates to the identification of the catalyst responsible for carrying out this process.

BACKGROUND OF THE INVENTION

Asymmetric hydrogenation using the Ru(II)-BINAP or Ru(II)-t-BINAP system (Ruthenium Complexes of 2,2'-bis(diphenylphosphino)-1,1'-binaphthyl or 2,2'-bis(di-p-tolylphosphino)-1,1'-binaphthyl) introduced by Noyori, et al. provides high enantioselectivity over a wide range of substrates with remarkable turnover (Noyori et al. *Acc. Chem. Res.*, 23, 345 (1990)). However, all reports concerning the reduction of β-ketoesters (Noyori et al., *J. Am. Chem. Soc.* 109, 5856 (1987)) suffer from the need for temperatures greater than 80° C. or hydrogen pressures greater than 6895 N/mm² where special apparatus is required (Kitamura et al., *Tetrahedron Lett.*, 32, 4163 (1991); Taber et al, *Tetrahedron Lett.*, 32, 4227 (1991); Keck et al, *J. Org. Chem.*, 56, 6606(1991)).

DETAILED DESCRIPTION OF THE INVENTION

Figure 1:
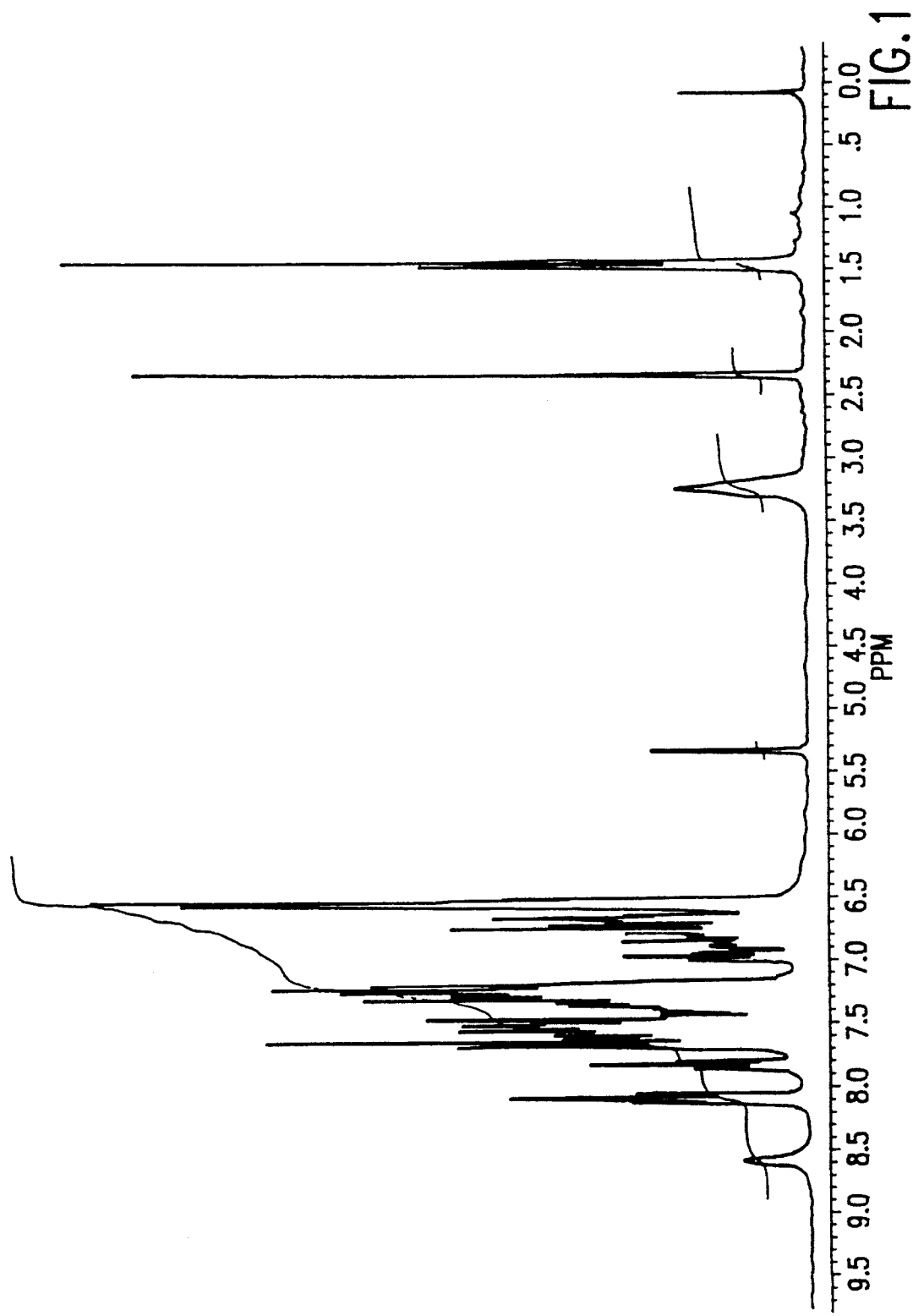
FIG. 1. 250 MHz ¹H NMR of [(C₂H₅)₂NH₂]⁺[Ru₂Cl₅((R)-BINAP)₂]⁻·CH₃Ph in CD₂Cl₂ at room temperature.

The novel process for the asymmetric reduction of β- or γ-ketoesters and β- or γ-ketoamides comprises adding a chiral ruthenium BINAP or t-BINAP catalyst, for example [(C₂H₅)₂NH₂]⁺[Ru₂Cl₅[(S)-BINAP]₂]⁻, [(C₂H₅)₂NH₂]⁺[Ru₂Cl₅[(S)-t-BINAP]₂]⁻, [RuCl(PhH)(BINAP)]Cl or [RuCl(PhH)(t-BINAP)]Cl catalyst to a solution of the β- or γ-ketoesters and β- or γ-ketoamides in a C₁₋₃ alkanol, preferably methanol, followed by the addition of a strong acid and reducing the β-or γ-ketoesters and β-or γ-ketoamides by agitation in the presence of hydrogen.

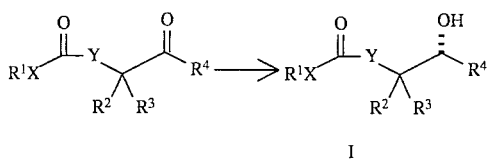

I wherein:

R¹ is straight or branched C₁–C₄ alkyl;

X is O or NR⁵;

Y is C(R²)₂ or a single bond;

R² is: H, or straight or branched C₁–C₆ alkyl;

R³ is: H, straight or branched C₁–C₆ alkyl, CH₂NHCOR⁶, or R¹ and R³ taken together form a lactone or cyclic amide of 5 to 7 atoms one of which is an oxygen or nitrogen;

R⁴ is:

CH₃, (a)

CH₂Cl, (b)

 (c)

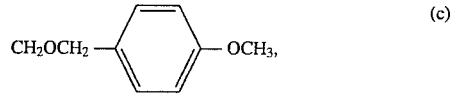 (d)

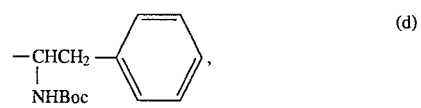 (e)

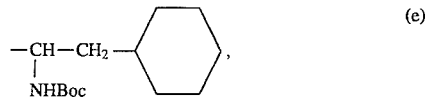 (f)

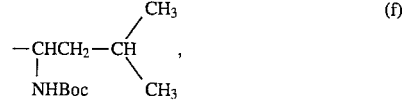 (g)

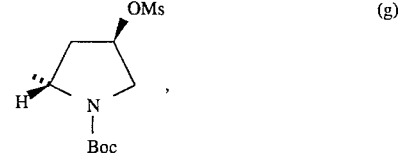 (h)

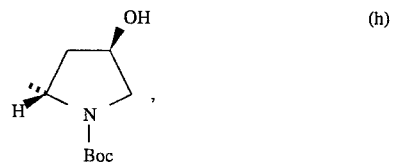 (i)

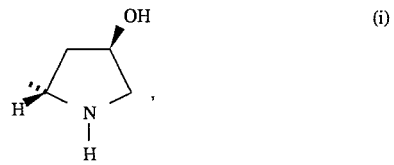 (j)

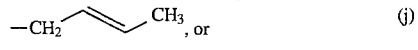

CH₂CH₂CH₂OCH₃; (k)

R³ and R⁴ taken together form a ring of 5 to 7 carbons, in which R³ and R⁴ represent a carbon chain of 3 to 5 carbons;

3

$R^5$ is H, straight or branched $C_1$–$C_4$ alkyl, or $CO_2$ $C_1$–$C_4$ alkyl; and $R^6$ is straight or branched $C_1$–$C_4$ alkyl, or O-$C_1$–$C_4$ alkyl, phenyl, O-benzyl.

Abbreviations

BINAP 2,2'-bis(diphenylphosphino)-1,1'-binaphthyl
t-BINAP 2,2'-bis(di-p-tolylphosphino)-1,1'-binaphthyl
BINAP in the instant application represents all chiral ligands of 2,2'-bis(diarylphosphino)-1,1'-binaphthyl and it is understood that although the specific stereochemistry is not recited that the ligand utilized is either the R- or the S-antipode. The selection of the R- or the S-BINAP ligand will determine the stereochemistry of the β- or γ-hydroxyesters and β-or γ-hydroxyamides produced.

* The asterik is being used to represent a specific enantiomer which is dependent on the stereochemistry of the BINAP employed.

| 1 N/mm² | is equivalent to approximately 0.145 psi |
| Boc | t-butyloxycarbonyloxy |
| Ms | methanesulfonyl |
| COD | Cyclooctadienyl |
| om | overlapping multiplet |

The amount of catalyst relative to amount of substrate over about 0.02 mole % is not critical, and excess catalyst will not seriously effect yield and enantiomeric purity, but amounts up to about 0.1 mole % are quite adequate.

The concentration of substrate in the alkanol is preferably about 0.5 to about 2.25M although the concentration is not critical. It is preferred that the alkanol solvent be deoxygenated before reduction such as by flowing nitrogen for several minutes.

The strong acid used in the novel process is about 0.1 to 10 mole % of HCl, $H_2SO_4$, $H_3PO_4$, $CH_3SO_3H$, or the like, preferably HCl, $H_2SO_4$, or $CH_3SO_3H$.

The reaction mixture is agitated by shaking or stirring and the reduction is accomplished at about 40°–50° C. and a hydrogen pressure of about 50 to about 1400 N/mm² until the required hydrogen uptake has occurred, usually in about 3–8 hours. Under the above-described conditions an enantiomeric excess >97% is routinely achieved for an achiral starting β or γ-ketoester and β or γ-ketoamide and the reaction is diastereoselective when the starting β- or γ-ketoester and β- or γ-ketoamide is chiral.

There is a dramatic dependence of the reaction on low levels of strong acid. A reaction mixture of a β- or γ-ketoester, or a β- or γ-ketoamide and catalyst, containing no acid, was exposed at 345 N/mm² (50 psi) of hydrogen at 50° C. for 24 hours with no hydrogen uptake. When 1 mole % HCl was added, the reaction went to completion in 3 hours. Sulfuric acid was equally effective. Significantly, the catalyst [RuCl(PhH)((R)-BINAP)]Cl, which contains no endogenous amine, also shows this acid dependence. A very low concentration of acid after neutralization of any basic impurities is required for maximum reaction rate. Any further increase in acid concentration provides no rate enhancement.

The catalyst is easily prepared using standard anaerobic techniques from commercially available (cyclooctadiene)ruthenium dichloride. Filtration of the product using a double ended filter provides a pure product, $[(C_2H_5)_2NH_2]^+$ $[Ru_2Cl_5(BINAP)_2]^-$ as a solvate, such as, benzene, toluene, xylene, chlorobenzene, or 1,2-, 1,3-, or 1,4-dichlorobenzene, etc.

4

Asymmetric reduction of a β-ketoester to the corresponding enantiomerically pure β-hydroxyester is an important synthetic step in the synthesis of a number of important useful chemical products such as:

1. The immunosuppressive agent, FK-506 (Jones et al. J. Org. Chem., 54, 17–19 (1989));
2. Colletal (Keck et al., J, Ore. Chem,, 56, 6606–6611 (1991));
3. Carnitine (Tetrahedron Letters, 29, 1555–1556 (1988));
4. Statine (Nishi et al., Tetrahedron Letters, 29, 6327–6330 (1988);
5. Gleosporine (Schreiber et al., J. Amer. Chem. Soc., 110, 6210–6218 (1988)).

Another important type of product involving an asymmetric reduction of a β-ketoester in its synthesis is a group of carbonic anhydrase inhibitors which are topically effective in the treatment of ocular hypertension and glaucoma associated therewith. This class of compounds has the general structure:

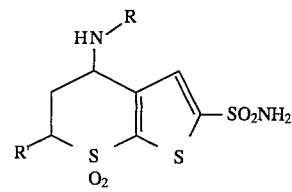

or a pharmaceutically acceptable salt thereof, wherein R is $C_{1-5}$ alkyl; and $R^1$ is hydrogen, $C_{1-3}$ alkyl or $C_{1-3}$ alkoxy-$C_{1-3}$ alkyl and are disclosed in U.S. Pat. No. 4,797,413, issued Jan. 10, 1989. The series of steps in the synthesis depicted below for the topical carbonic anhydrase inhibitor, wherein R is defined as n-propyl and R' is defined as methoxypropyl, is representative of the process of this invention.

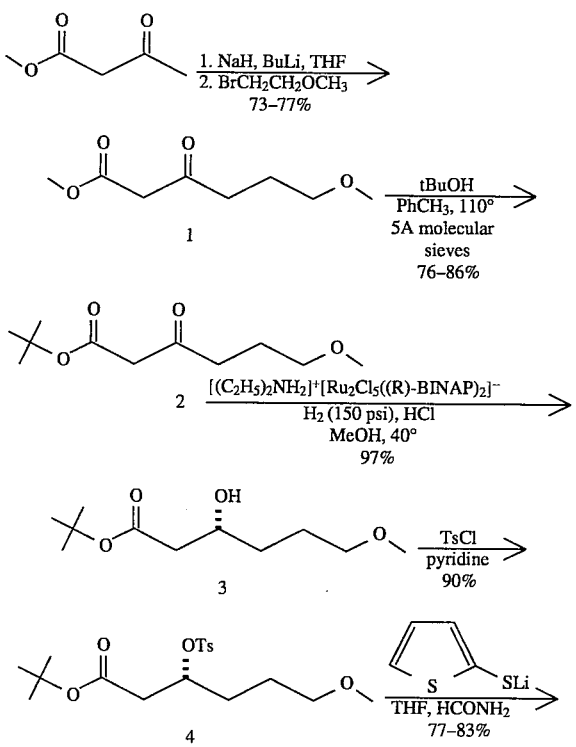

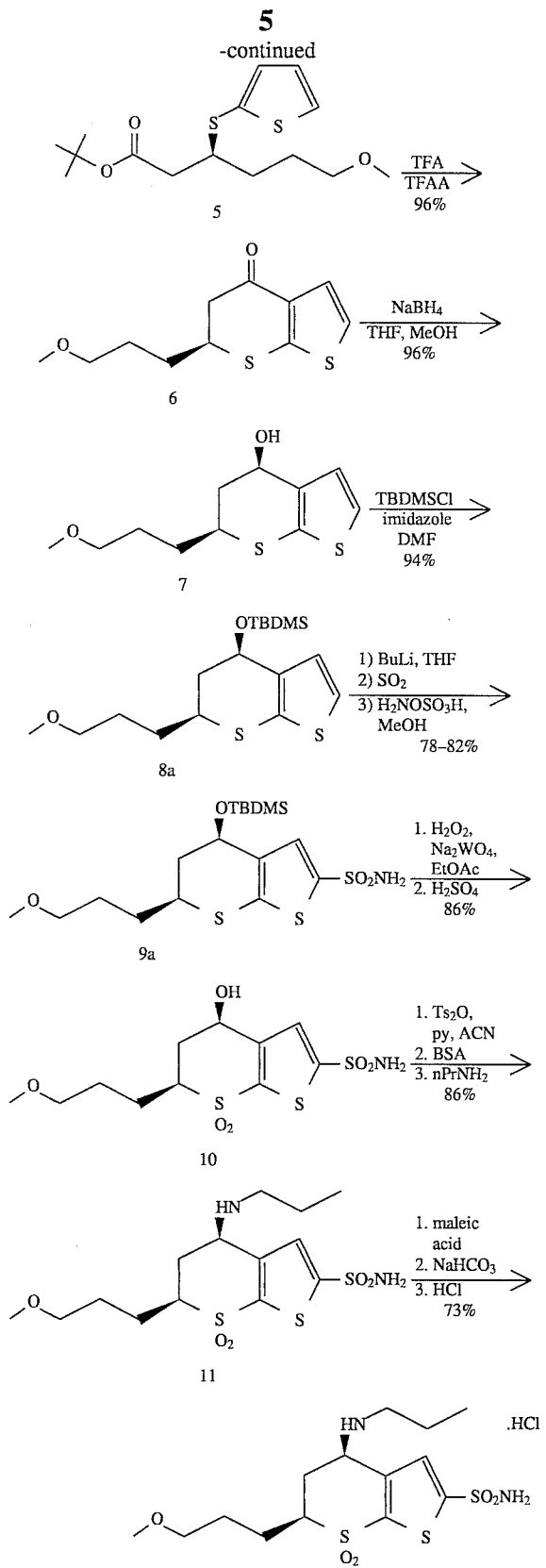

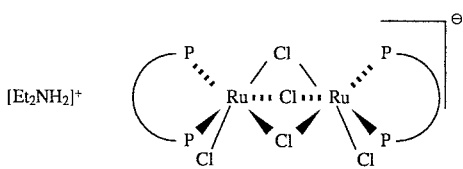

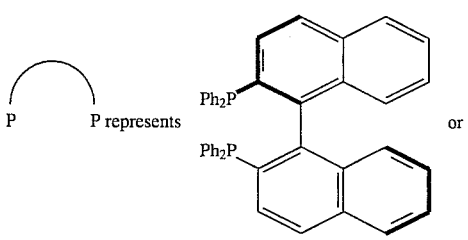

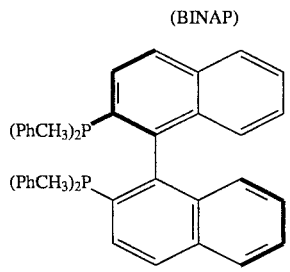

The novel process of this invention is depicted as 2→3 in the above reaction scheme. The enantiomerically pure alcohol produced in this step is responsible for installing the optical activity of the carbonic anhydrase inhibitors. Its activation and displacement with inversion provides the optically pure 5 which can be cyclized to the key intermediate 6 which contains the carbon skeleton of these compounds.

The following examples further illustrate the use of the process for the preparation of the compounds of Formula I and the use of this catalyst in this process and, as such, are not be considered or construed as limiting the invention recited in the appended claims.

EXAMPLE 1

Catalyst Preparation

Step A: Preparation of $[(C_2H_5)_2NH_2]^+[Ru_2Cl_5((R)\text{-BINAP})_2]^- \cdot CH_3Ph$ Structure 12

(Cyclooctadienyl)ruthenium dichloride (214 mg, 0.76 mmol) and (R)-BINAP (500 mg, 0.80 mmol), were placed in a 50 mL round bottom flask and connected to a double ended filter (Kontes #215500-6044) with a 100 mL round bottom flask at the opposite end. Vacuum grease was used to ensure an air-tight seal. Rubber bands were a simple and effective way of holding the apparatus together. The entire apparatus was evacuated and filled with nitrogen. Dry toluene (17 mL) and dry triethylamine (1.7 mL), which had been deoxygenated with flowing nitrogen for several minutes, were added via the lower side arm. The vessel was sealed and the mixture heated to 140° C. producing a deep brick red colored solution. After 4 hours the apparatus was allowed to cool to room temperature with vigorous stirring while the catalyst precipitated. The apparatus was vented to nitrogen and inverted to filter the product using vacuum on the lower side arm and nitrogen on the upper. The precipitate was washed with deoxygenated toluene (17 mL), and the flask containing the filtrate was exchanged for an empty one. ($^{31}$P NMR showed that the filtrate contained none of the desired product.) The entire apparatus was put under vacuum and the product was dried overnight to give 470 mg (75%) of a dark red solid:

$^1$H NMR (CD$_2$Cl$_2$, 400.13 MHz) ∂8.53(br s, 2H), 8.07 (t, J=8.8 Hz, 4H), 7.82 (t, J=8.3 Hz, 2H), 7.65 (m, 6H), 7.55 (m, 4H), 7.47 (m, 4H), 7.4–7.1 (m, 18H), 6.95 (m, 2H), 6.84 (t, J=7.4 Hz, 2H), 6.8–6.7 (om, 4H), 6.7–6.6 (om, 4H), 6.6–6.5 (om, 12H), 3.24 (br m, 6H), 2.3 (s,3H), 1.45 (t, J=7.3 Hz, 9H) [See FIG. 1 for $^1$H NMR spectrum]; $^{31}$P NMR (CD$_2$Cl$_2$, 161.98 MHz) ∂56.5 (d, J=38.0 Hz), 52.3 (d, J=38.0 Hz); Analysis Calc'd for C$_{99}$H$_{84}$Cl$_5$NP$_4$Ru$_2$: C 66.39, H 4.73, N 0.78, Cl 9.90, P 6.87; Found C 66.06, H 4.74, N 0.74, Cl 9.79, P 6.91.

Figure 2A:
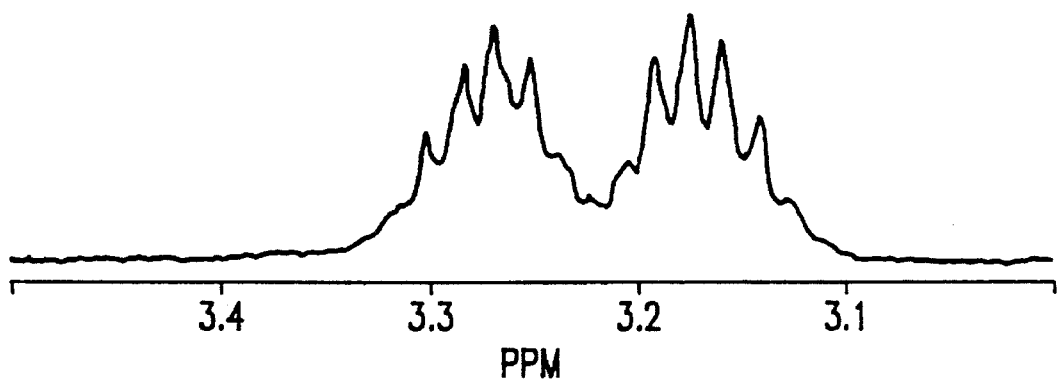
FIG. 2. Expansion of the 3.0 ppm to 3.5 ppm region of 400.13 MHz ¹H NMR of [(C₂H₅)₂NH₂]⁺[Ru₂Cl₅((R)-BINAP)₂]⁻·CH₃Ph in CD₂Cl₂ at −40° C. (a) is the fully coupled spectrum of this region; (b) is the decoupled spectrum of this region resulting from the irradiation of the peak at 8.53 ppm; and (c) is the decoupled spectrum of this region resulting from the irradiation of the peak at 1.41 ppm.
Figure 2B:
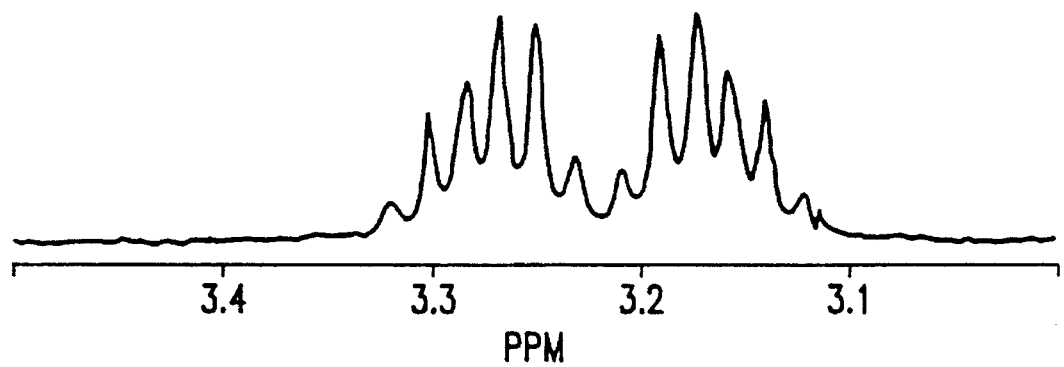
Figure 2C:
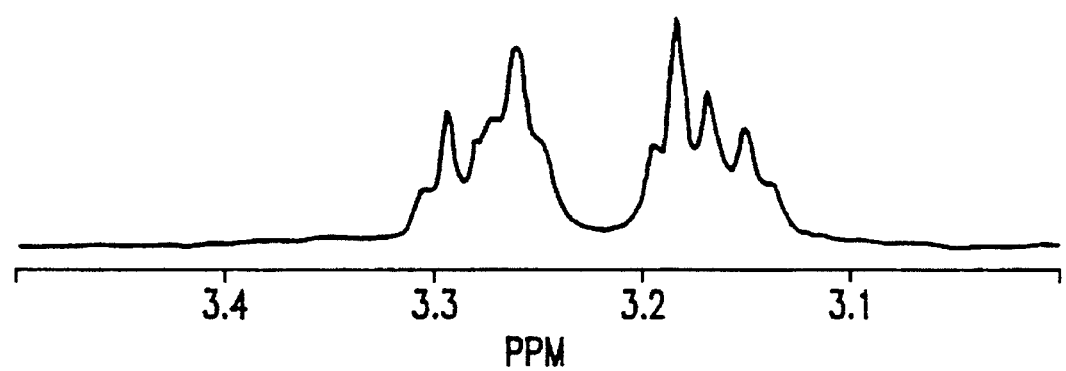

Decoupling and spiking experiments unequivocally established the presence of diethylammonium ion. At –40° C. the methylene protons of the diethylammonium appear as two multiplets at 3.2 ppm. [See FIG. 2 (a) for $^1$H NMR spectrum] When the triplet at 1.4 ppm was irradiated the signal at 3.2 ppm appears as two doublets of triplets. [See FIG. 2 (c) for $^1$H NMR spectrum] When the broad singlet at 8.53 ppm is irradiated the signal at 3.2 ppm appears as two doublets of quartets. [See FIG. 2 (b) for $^1$H NMR spectrum]. When diethylamine was added to the solution the signal at 3.2 ppm was seen to diethylamine was added to the solution the signal at 3.2 ppm was seen to coalesce with the diethylamine signal. Triethylamine did not produce this behavior.

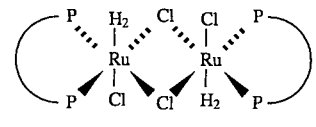

13

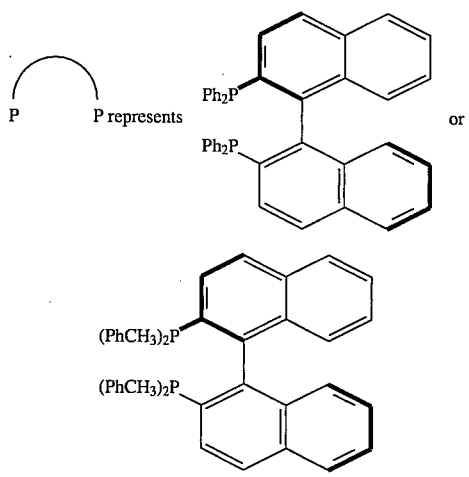

P⌒P represents or

Step B: Preparation Of Ru$_2$Cl$_4$((R)-BINAP)$_2$ Structure 13

The catalyst 12 (12 mg, 6.7 µmol) was loaded into a gas tight NMR tube (available from Wilmad) which was evacuated and refilled with nitrogen. Dry methylene chloride-d$_2$ (0.8 mL) was deoxygenated by bubbling with nitrogen for 2 minutes. It was added with a thin needle by partially unstoppering the tube while nitrogen was flowing through the plug, flushing air away from its mouth. The atmosphere over the solvent was immediately purged by carefully evacuating and refilling with nitrogen. Catalyst dissolution was aided by the use of sonication or a vortex mixer. Methanesulfonic acid (4 µL, 62 µmol) was added to give the desired product:

$^1$H NMR (CD$_2$Cl$_2$, 400.13 MHz) ∂8.14 (d, J=7.9 Hz, 2H), 8.10 (d,d, J=9.1,1.6 Hz, 2H), 7.73 (d, J=7.9 Hz, 2H), 7.65 (t, J=7.5 Hz, 2H), 7.59 (m, 2H), 7.55–7.35 (om, 22H), 7.26–7.09 (om, 18H), 6.82–6.77 (om, 4H), 6.15 (m, 4H), 6.05 (d, J=8.7 Hz, 2H), 5.83 (dd, J=12.3, 7.9 Hz, 4H); $^{31}$P NMR (CD$_2$Cl$_2$, 161.98 MHz) ∂62.6 (d, J=40.3 Hz), 13.7 (d, J=40.3 Hz).

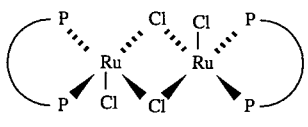

14

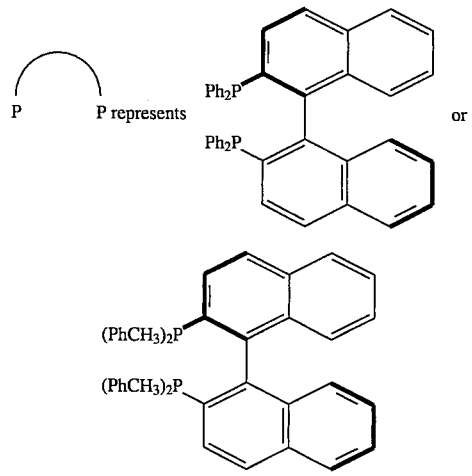

P⌒P represents or

Step C: Preparation of [Ru$_2$Cl$_4$((R)-BINAP)$_2$(H$_2$)$_2$] Structure 14

A gas tight NMR tube containing 13 was put under a hydrogen atmosphere by evacuating and filling with hydrogen at a positive pressure of 8 psi. To ensure saturation of the solution, the tube was put on a vortex mixer while attached to the manifold and stirred for 10 minutes.

The $^1$H and $^{31}$P spectra indicate that the hydrogen adduct is a mixture of conformational or configurational forms.

$^1$H NMR (CD$_2$Cl$_2$, 400.13 MHz) ∂8.2–5.8 (om), –9.85, –10.08, –10.2, –10.88, –11.12, –11.52; $^{31}$P NMR (CD$_2$Cl$_2$, 161.98 MHz) ∂58.8 (d, J=29.7 Hz), 56.2 (d, J=30.4 Hz), 55.1 (d, J=32.4 Hz), 54.9 (d, J=31.7 Hz), 51.7 (d, J=29.7 Hz), 50.9 (d, J=31.0 Hz), 50.5 (d, J=33.1 Hz), 48.5 (d, J=31.7 Hz), 47.2 (d, J=30.4 Hz), 46.7 (d, J=33.1 Hz), 46.4 (d, J=32.4 Hz), 44.9 (d, J=31.0 Hz).

The species 13 and 14 have been shown to be active catalysts as demonstrated in the following experiment:

To the above mixture methyl acetoacetate (20 µL) and methanol (100 µL) were added, and the NMR signals for species 14 immediately disappeared and methyl 4-hydroxybutyrate and 13 appeared. After standing over night, the hdroxy product was isolated. Examination of the (S)-Mosher ester of methyl 4-hydroxybutyrate showed the product to be >90% enantiomeric excess.

EXAMPLE 2

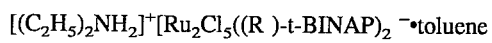

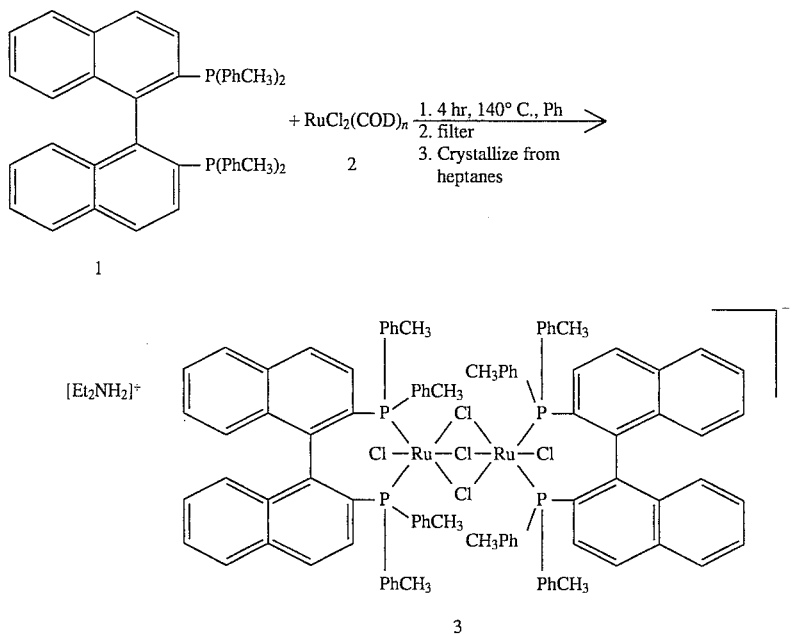

To a 50 mL round bottom flask was charged 500 mg of (S)-t-BINAP 1, 197 mg of RuCl$_2$[COD]$_n$ polymer 2, 1.4 mL of Et$_3$N and 17 mL of degassed toluene. The flask was sealed and heated to 140° C. for 6 hours. The dark red homogeneous solution was cooled to ambient temperature and the solution was concentrated under reduced pressure to 8 mL. Then 12 mL of heptanes was added and the solution was stirred for one hour. The Ruthenium polymer precipitated and was filtered off via double ended filter. The homogeneous solution was concentrated under reduced pressure to 8 mL. Then 12 mL of heptanes was added and the solution was stirred for one hour. The catalyst precipitated and was filtered off via doubled ended funnel (schlenk ware). The precitate was dried under vacuum, giving 300 mg of light yellow solid for 55% yield.

EXAMPLE 3

[(C$_2$H$_5$)$_2$NH$_2$]$^+$[Ru$_2$Cl$_5$((R)-BINAP)$_2$]$^-$•xylene (Cyclooctadienyl)ruthenium dichloride (2.14 g, 7.6 mmol) and (R)-BINAP (5.00 g, 8.0 mmol) were placed in a 50 mL round bottom flask and connected to a double ended filter (Kontes #215500-6044) with a 1000 mL round bottom flask at the opposite end. Vacuum grease was used to ensure an air-tight seal. The entire apparatus was evacuated and filled with nitrogen. Dry xylenes (170 mL) and dry triethylamine (17 mL), which had been deoxygenated with flowing nitrogen for several minutes, were added via the lower side arm. The mixture was heated to 140 ° C. producing a deep brick red colored solution. After 4 hours the apparatus was allowed to cool to room temperature with vigorous stirring while the catalyst precipitated. The apparatus inverted to filter the product using vacuum on the lower side arm and nitrogen on the upper. The precipitate was washed with deoxygenated xylene (17 mL), and the flask containing the filtrate was exchanged for an empty one. The entire apparatus was put under vacuum and the product was dried overnight to give 440 mg (69%) of a dark red solid:

$^1$H NMR (CD$_2$Cl$_2$, 400.13 MHz) ∂8.07 (t, J=8.8 Hz, 4H), 7.82 (t, J=8.3 Hz, 2H), 7.65 (m, J=8.3 Hz, 6H), 7.55 (m, 4H), 7.47 (m, 4H), 7.4–7.1 (om, 20H), 6.95 (m, 2H), 6.84 (t, J=7.4 Hz, 2H), 6.8–6.7 (om, 4H), 6.7–6.6 (om, 4H), 6.6–6.5 (om, 12H), 3.24 (m, 6H), 2.5–2.3 (3 singlets, 6H), 1.45 (t, J=7.3 Hz, 9H); $^{31}$P NMR (CD$_2$Cl$_2$, 161.98 MHz) ∂56.5 (d, J=38.0 Hz), 52.3 (d, J=38.0 Hz).

EXAMPLE 4 t-Butyl 3-hydroxy-6-methoxy hexanoate

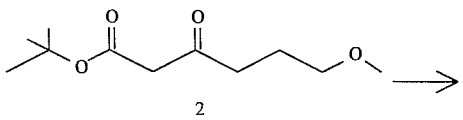

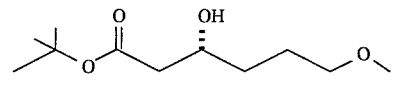

Step A: Preparation of t-butyl 3-keto-6-methoxy hexanoate (Ketoester 2)

The dianion of methyl acetoacetate, generated with sodium hydride and n-butyl lithium in THF at −15° C., is alkylated with 1.2 equivalents of bromoethyl methyl ether. The reaction proceeds in 6–8 hours to a level of 3 wt % residual starting material and is worked up with methyl t-butyl ether (MTBE) and saturated ammonium chloride solution. Residual methyl acetoacetate (b.p. 159° C.) is removed by flushing crude product with four to seven volumes of xylene to provide the alkylated ketoester containing <0.25 wt % methyl acetoacetate in 73–77% yield.

The methyl ester is transesterified to the t-butyl ester in 95:5-toluene:t-butanol by refluxing the solvent through 5A molecular sieves. The boiling point of the solvent mixture is 107°–111° C., well above the boiling point of t-butanol, which can be slowly lost from the vessel and must be replaced as needed. After concentration, the t-butyl ester is produced in 95% yield with <1% remaining methyl ester.

Step B: Preparation of t-butyl 3-hydroxy-6-methoxy hexanoate (β-hydroxyester 3)

The hydrogenation catalyst [(C$_2$H$_5$)$_2$NH$_2$]$^+$[Ru$_2$Cl$_5$((R)-BINAP)$_2$]$^-$ is not commercially available and must be prepared from [RuCl$_2$(COD)]$_n$ and (R)-BINAP (see Example 1). Twenty gram batches are conveniently prepared in a 1L flask. Use of a double ended filter allows convenient isolation of the product on this scale. The catalyst, which can be handled and weighed in air, should be stored under nitrogen.

Asymmetric reduction of ketoester 2 is conducted in methanol at 45° C. under 1034 N/mm$^2$ (150 psi) hydrogen with 0.09 mol % (0.4 wt %) [(C$_2$H$_5$)$_2$NH$_2$]$^+$[Ru$_2$Cl$_5$((R)-BINAP)$_2$]$^-$. The reaction mixture should be deoxygenated with nitrogen and the vessel thoroughly evacuated and flushed with nitrogen prior to pressurization with hydrogen. The reaction is exothermic and requires periodic cooling to maintain the temperature at 45°. After 4 hours hydrogen uptake is complete and the catalyst is precipitated with hexane and filtered away. Concentration provides a >97% yield of the alcohol whose enantiomeric excess is determined to be 97% by proton NMR analysis of the derived Mosher ester.

The hydrogenation reaction is very susceptible to the presence of basic impurities and acidification of these with small amounts of strong acid is required.

Transesterification during the reaction can result from either high temperatures or the presence of excess amounts of acid. Thus, the reaction temperature should be kept at 45° and the minimum possible amount of HCl should be used.

EXAMPLE 5 tert-Butyl 3(R)-hydroxybutyrate

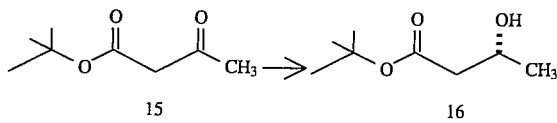

tert-Butyl acetoacetate [15] (14.5 g, 90 mmol) and methanol (30 mL) were mixed and deoxygenated with flowing nitrogen for 5 minutes in a septum covered Parr shaker bottle. The catalyst prepared as described above (36 mg, 0.02 mmol) was added along with 2N HCl (0.041 mL, 0.082 mmol). The mixture was transferred to a standard Parr shaker apparatus and flushed by evacuating and refilling with nitrogen and then hydrogen several times. The apparatus was heated at 40° C. with shaking under 50 psi of hydrogen. After 20 min the reaction became a homogeneous clear yellow solution which took up hydrogen for approximately eight hours. At this time the reaction was complete and the mixture was cooled and diluted with hexane (30 mL) to precipitate the catalyst, which was filtered away. The filtrate was concentrated to give tert-butyl 3(R)-hydroxybutyrate [16] (14.5 g, 97%).

EXAMPLE 6 tert-Butyl 3(R)-hydroxybutyrate

Following the procedure described in Example 3 with the exception that 2N H$_2$SO$_4$ was substituted for the 2N HCl tert-butyl acetoacetate was reduced to the titled product.

EXAMPLE 7

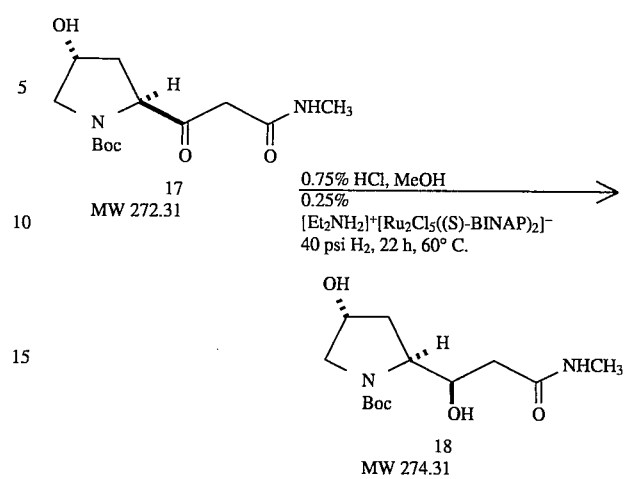

In a 25 mL round bottom flask with a septum the β-keto amide 17 (1 g) was dissolved in methanol (4 mL). The solution was deoxygenated with nitrogen for 20 minutes and then the finely ground (C$_2$H$_5$)$_2$NH$_2$]$^+$[Ru$_2$Cl$_5$((S)-BINAP)$_2$]$^-$ catalyst (15.5 mg) (prepared as described in Example 1) was added. The solution was degassed with nitrogen for 5 minutes and 2N hydrochloric acid (0.092 mL) was added. The mixture was cannulated into the reaction pressure vessel. The apparatus was heated at 60° C. with shaking under 40 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid.

The crude reaction mixture gave a 87:13 ratio of the R:S hydroxy esters.

The yield was 100%.

EXAMPLE 8

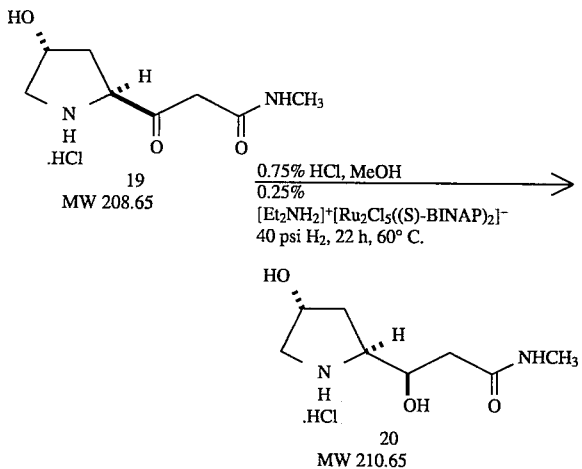

In a 25 mL round bottom flask with a septum the β-keto amide HCL salt 19 (1 g) was dissolved in methanol (16 mL). The solution was deoxygenated with nitrogen for 20 minutes and then the finely ground [(C$_2$H$_5$)$_2$NH$_2$]$^+$[Ru$_2$Cl$_5$((S)-BINAP)$_2$]$^-$ catalyst (20.2 mg) (prepared as described in Example 1 ) was added. The solution was degassed with nitrogen for 5 minutes and 2N hydrochloric acid (0.120 mL) was added. The mixture was cannulated into the reaction pressure vessel. The apparatus was heated at 60° C. with shaking under 40 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid. The crude reaction mixture gave a 97:3 ratio of the R:S hydroxy amides.

The yield was 80%.

EXAMPLE 9

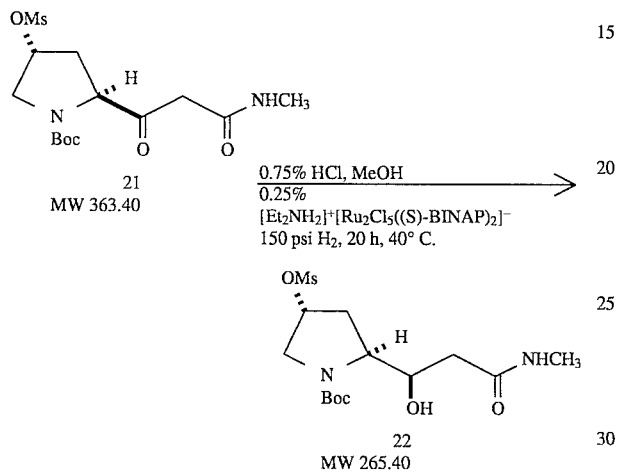

In a 25 mL round bottom flask with a septum the β-keto amide mesylate 21 (0.957 g) was dissolved in methanol (2.5 mL). The solution was deoxygenated with nitrogen for 20 minutes and then the finely ground [(C$_2$H$_5$)$_2$NH$_2$]$^+$ [Ru$_2$Cl$_5$((S)-BINAP)$_2$]$^-$ catalyst (11 mg) (prepared as described in Example 1) was added. The solution was degassed with nitrogen for 5 minutes and 2N hydrochloric acid (0.020 mL) was added. The mixture was cannulated into the reaction pressure vessel. The apparatus was heated at 40° C. with stirring under 150 psi of hydrogen for 20 hours.

After 20 h the reaction mixture was removed from the reaction pressure vessel. The vessel was rinsed with methanol (3 mL) which was combined with the reaction mixture. The solution was concentrated under reduced pressure to an off-white solid. The crude reaction mixture gave a 91:9 ratio of the R:S hydroxy amide mesylates. The yield was 80%.

EXAMPLE 10

(R)-Trans-2-Methoxycarbonylcyclopentanol

2-Methoxycarbonyl-cyclopentanone (4.26 g) was dissolved in methanol (5 mL) and 0.1 mL 1N HCl was added. The mixture was deoxygenated, 1 (36 mg) was added and the mixture was exposed to hydrogen at 40 psi and 40° in a Parr shaker apparatus. After 6 h the reaction was complete, providing a single product (4.10 g) in >95% ee: $^1$H NMR (CDCl$_3$, 250 MHz) 4.40 (q, J=7.5 Hz, 1H), 3.71 (s, 3H), 2.65 (q, J=7.2 Hz, 1H), 2.1–1.5 (m, 6H).

EXAMPLE 11

Methyl 3-Hydroxy-2-methylbutyrate

Methyl 2-methylacetoacetate was hydrogenated under the conditions set forth in Example 2 or 3, to give a 6:4 mixture of trans:cis product. Enantiomeric excess of the major isomer was >97%.

EXAMPLE 12

Methyl 5-(R)-hydroxyvalerate

A mixture of methyl levulinate (10.0 g, 77 mmol), methanol (10 mL) and concentrated HCl (0.4 mL) was deoxygenated with bubbling nitrogen for 2 minutes. [(C$_2$H$_5$)$_2$NH$_2$]$^+$ [Ru$_2$Cl$_5$((R)-BINAP)$_2$]$^-$ (50 mg) was added and the mixture placed in a standard Parr shaker apparatus. After evacuating and flushing with nitrogen three times, the mixture was evacuated and exposed to 40 psi hydrogen pressure at 40° C. for 48 h. The solvent was removed in vacuo to give the product (9.90g, 99% yield) which was identical to a commercially available (Aldrich) racemic sample by $^1$H NMR. The optical purity was shown to be 99:1 by obtaining proton NMR spectrum of the product (1 mL) and (S)-(+)-2,2,2-trifluro-1-(9-anthryl)ethanol (27 mg) in CDCl$_3$. Peak assignments were made by spiking with a sample of the racemate. Methyl 5-(R)-hydroxyvalerate spontaneously lactonizes to give 5-(R)-γ-valerolactone.

EXAMPLE 13

Ethyl 3-hydroxybutyrate

This was prepared from ethyl acetoacetate in ethanol according to the procedure of Example 4 or 5. Enantiomeric excess was measured to be 97%. $^1$H NMR (CDCl$_3$, 250 MHz) 4.20 (m, 1H), 4.10 (q, J=7.5 Hz, 1H), 2.51 (m, 2H), 1.2 (m, 5H).

What is claimed is:

1. A compound of structural formula:

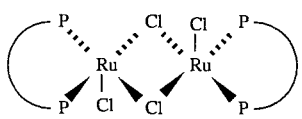

wherein:

represents 2,2'-bis(diphenylphosphino)-1,1'-binaphthyl or 2,2'-bis(di-p-tolylphosphino)-1,1'-binaphthyl.

2. A compound of structural formula:

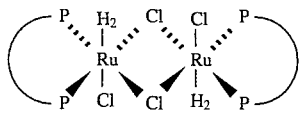

wherein:

represents 2,2'-bis(diphenylphosphino)-1,1'-binaphthyl or 2,2'-bis(di-p-tolylphosphino)-1,1'-binaphthyl.

3. A compound of structural formula:
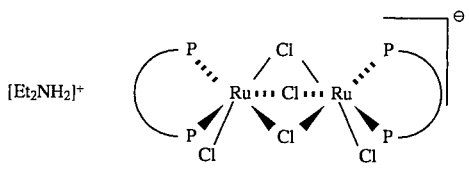
or solvates thereof,
wherein;
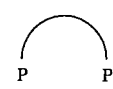
represents 2,2'-bis(diphenylphosphino)-1,1'-binaphthyl or 2,2'-bis(di-p-tolylphosphino)-1,1'-binaphthyl.
* * * * *

UNITED STATES PATENT AND TRADEMARK OFFICE
CERTIFICATE OF CORRECTION

PATENT NO. : 5,596,113
DATED : January 21, 1997
INVENTOR(S) : Alan W. Douglas, Lisa DiMichele, Steven A. King and Thomas R. Verhoeven It is certified that error appears in the above-indentified patent and that said Letters Patent is hereby corrected as shown below:

In Column 14, in Claim 1, between lines 40-45, after the structure, please insert:

or solvates thereof,

In Column 14, in Claim 2, between lines 55-60, after the structure, please insert:

or solvates thereof,

Signed and Sealed this

Twenty-ninth Day of April, 1997

*Attest:*

BRUCE LEHMAN

*Attesting Officer*      Commissioner of Patents and Trademarks